US012601731B2

(12) United States Patent
Srinivasan et al.

(10) Patent No.: US 12,601,731 B2
(45) Date of Patent: Apr. 14, 2026

(54) METHOD TO DETERMINE API GRAVITY OF SULFUR-RICH MARINE OILS USING AROMATIC COMPOUND CHEMISTRY

(71) Applicant: ARAMCO SERVICES COMPANY, Houston, TX (US)

(72) Inventors: Poorna Srinivasan, Houston, TX (US); David Jacobi, Houston, TX (US); Estefania M. Endara Arguello, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 368 days.

(21) Appl. No.: 18/496,621

(22) Filed: Oct. 27, 2023

(65) Prior Publication Data

US 2025/0137988 A1 May 1, 2025

(51) Int. Cl.
*G01N 33/28* (2006.01)
*G01N 30/86* (2006.01)

(52) U.S. Cl.
CPC ..... *G01N 33/2823* (2013.01); *G01N 30/8665* (2013.01); *G01N 30/8679* (2013.01)

(58) Field of Classification Search
CPC ........... G01N 30/8631; G01N 30/8658; G01N 30/8665; G01N 30/8679; G01N 33/2823
See application file for complete search history.

(56) References Cited

U.S. PATENT DOCUMENTS 4,463,096 A 7/1984 Hughes
5,780,850 A * 7/1998 DeLaune ............. G01N 33/241
250/301

(Continued)

FOREIGN PATENT DOCUMENTS

CN 101413930 A * 4/2009
CN 104730595 B 11/2015
(Continued)

OTHER PUBLICATIONS

Meijun Li, et al., "Oil maturity assessment using maturity indicators based on methylated dibenzothiophenes;" Petroleum Science; May 7, 2014 (17 pages).

(Continued)

*Primary Examiner* — John Fitzgerald

(74) *Attorney, Agent, or Firm* — Osha Bergman Watanabe & Burton LLP

(57) ABSTRACT

A method of determining an API gravity of a crude oil includes obtaining a reservoir sample containing the crude oil, separating an aromatic fraction from the reservoir sample, analyzing the aromatic fraction using a gas chromatography mass spectrometry (GC-MS) instrument, determining peak areas and a ratio of 4-methyldibenzothiophene and 1-methyldibenzothiophene, and determining the API gravity of the crude oil in the reservoir sample using an empirical correlation between API gravity and the ratio of 4-methyldibenzothiophene to 1-methyldibenzothiophene. A method of determining productivity of a region of a reservoir includes determining an API gravity of a crude oil in the sample from the region of the reservoir using an empirical correlation between API gravity and the ratio of 4-methyldibenzothiophene to 1-methyldibenzothiophene, and based on the API gravity of the sample, determining the productivity of the region of the reservoir.

12 Claims, 4 Drawing Sheets

300

301 — Obtain a sample from the region

303 — Separate an aromatic fraction from the sample

305 — Analyze the aromatic fraction using GC-MS

307 — Determine peak areas of 4-MDBT and 1-MDBT

309 — Determine a 4-MDBT:1-MDBT ratio

311 — Determine the API gravity using an empirical correlation

313 — Determine the productivity of the region

(56)                References Cited

U.S. PATENT DOCUMENTS

| | | | |
|---|---|---|---|
| 6,500,219 | B1 | 12/2002 | Gunnerman |
| 6,708,758 | B2 | 3/2004 | de Rouffignac et al. |
| 10,031,121 | B2 * | 7/2018 | Koseoglu ............... G01N 21/33 |
| 10,240,098 | B2 | 3/2019 | Randhava et al. |
| 10,641,750 | B2 * | 5/2020 | Holba .................... G01N 30/88 |
| 10,703,998 | B2 | 7/2020 | Koseoglu |
| 11,639,921 | B2 * | 5/2023 | Henderson ......... G01N 21/3504 |
| | | | 73/152.01 |
| 2003/0051988 | A1 | 3/2003 | Gunnerman et al. |
| 2022/0055022 | A1 | 2/2022 | Song et al. |
| 2024/0125720 | A1 * | 4/2024 | Cabral Da Silva .......................... |
| | | | G01N 33/2823 |

FOREIGN PATENT DOCUMENTS

| | | | |
|---|---|---|---|
| KR | 100885497 B1 | 2/2009 | |
| RU | 2667174 C1 | 9/2018 | |
| WO | WO-2014022794 A2 * | 2/2014 | ......... G01N 30/8682 |

OTHER PUBLICATIONS

Saroj K. Panda, et al., "Characterization of aromatic hydrocarbons and sulfur heterocycles in Saudi Arabian heavy crude oil by gel permeation chromatography and ultrahigh resolution mass spectrometry;" Fuel; vol. 235, pp. 1420-1426; Jan. 1, 2016 (7 pages).

Abdullah, F. H. and Connan, J. (2002) Geochemical study of some Cretaceous rocks from Kuwait: comparison with oils from Cretaceous and Jurassic reservoirs. Organic Geochemistry 33, 125-148. (24 pages).

Kobraei, M., Rabbani, A., Taati, F. (2019) Upper Jurassic-Lower Cretaceous source-rock evaluation and oil-source rock correlation in the Abadan Plain, Southwest Iran. Geochemistry International 57, 790-804. (15 pages).

Manshad, A. K., Pashaki, R. S., Ali, J. A., Iglauer, S., Memariani, M., Akbari, M., Keshavarz, A. (2021) Geochemical study of the early cretaceous Fahliyan oil reservoir in the northwest Persian Gulf. Journal of Petroleum Exploration and Production Technology 11, 2435-2447. (13 pages).

Morales-Bautista, C.M., Adams, R.H., Guzman-Osorio, F., Marin-Garcia, D. (2013) Dilution-extrapolation hydrometer method for easy determination of API gravity of heavily weathered hydrocarbons in petroleum contaminated soil. Energy and Environment Research, 3, 115-124. (10 pages).

Peters, K. E., Walters, C. C., Moldowan, J. M. (2005) The Biomarker Guide: vol. 1, Biomarkers and Isotopes in the Environment and Human History. Cambridge University Press (488 pages).

Santamaria-Orozco, D., Horsfield, B., Di Primo, R., Welte, D. H. (1998) Influence of maturity on distributions of benzo- and dibenzothiophenes in Tithonian source rocks and crude oils, Sonda de Campeche, Mexico. Organic Geochemistry 28, 423-439. (17 pages).

Srinivasan, P., Jacobi, D., Atwah, I., Karg, H., Azzouni, A. (2022a) Integration of methyldibenzothiophene and pyrolysis techniques to determine thermal maturity in sulfur-rich Type II-S source rocks and oils. Organic Geochemistry 163, 104333. (17 pages).

Srinivasan, P., Jacobi, D., Atwah, I., Karg, H., Azzouni, A. (2022b) Generation temperatures for oils sourced from sulfur-rich kerogens using aromatic and light hydrocarbon isomers. Marine and Petroleum Geology 146, 105917(12 pages).

Wieclaw, D. (2011) Origin of liquid hydrocarbons accumulated in the Miocene strata of the Polish Carpathian foredeep and its Paleozoic-Mesozoic basement. Annales Societatis Geologorum Poloniae 81, 443-458. (17 pages).

Wieclaw, D., Kotarba, M. J., Kowalski, A., Koltun, Y. V. (2012) Origin and maturity of oils in the Ukranian Carpathians and their Mesozoic basement. Geological Quarterly 56, 153-168. (16 pages).

Orr, W.L. (2001) Evaluating kerogen sulfur content from crude oil properties: Cooperative Monterey Organic Geochemistry Study, in C.M. Isaacs, and J. Rullkötter, eds., The Monterey Formation: From rocks to molecules: New York, Columbia University Press, p. 348-367. (20 pages).

Hegazi, A. H. and Andersson, J. T. (2007) Limitations to GC-MS determination of sulfur-containing polycyclic aromatic compounds in geochemical, petroleum, and environmental investigations. Energy & Fuels 21, 3375-3384. (10 pages).

Strubinger, A., Ehrmann, U., Leon, V. (2012) Using the gas pycnometer to determine API gravity in crude oils and blends. Energy and Fuels, 25, 6863-6868. (6 pages).

Ruh, E. L., Moran, J. J., Thompson, R. D. (1959) Measurement problems in the instrument industry and laboratory apparatus fields. In Systems and Units, National and International Aspects (ed. Carl F. Kayan). Washington, D.C.: American Association for the Advancement of Science, pp. 29. (8 pages).

Zhang, S., Huang, H., Su, J., Liu, M., Wang, X., Hu, J. (2015) Geochemistry of Paleozoic marine petroleum from the Tarim Basin, NW China: Part 5. Effect of maturation, TSR and mixing on the occurrence and distribution of alkylbenzothiophenes. Organic Geochemistry 86, 5-18. (17 pages).

Orr, W.L. (1986) Kerogen/asphaltene/sulfur relationships in sulfur-rich Monterey oils: Organic Geochemistry, v. 10, p. 499-516. (18 pages).

Baskin, D. K. and Peters, K. E. (1992) Early generation characteristics of a sulfur-rich Monterey kerogen. AAPG Bulletin 76, 1-13. (13 pages).

Al-Ameri, T. K., Al-Marsoumi, S. W., Al-Musawi, F. A. (2015) Crude oil characterization, molecular affinity, and migration pathways of Halfaya oil field in Mesan Governorate, South Iraq. Arabian Journal of Geoscience 8, 7041-7058. (18 pages).

Chiaberge, S., Fiorani, T., Cesti, P. (2011) Methyldibenzothiophene isomer ratios in crude oils: Gas chromatography tandem mass spectrometry analysis. Fuel Processing Technology 92, 2196-2201. (6 pages).

* cited by examiner

300

301 — Obtain a sample from the region

303 — Separate an aromatic fraction from the sample

305 — Analyze the aromatic fraction using GC-MS

307 — Determine peak areas of 4-MDBT and1-MDBT

309 — Determine a 4-MDBT:1-MDBT ratio

311 — Determine the API gravity using an empirical correlation

313 — Determine the productivity of the region

METHOD TO DETERMINE API GRAVITY OF SULFUR-RICH MARINE OILS USING AROMATIC COMPOUND CHEMISTRY

BACKGROUND

Determinations of oil gravities are known to be extremely valuable in the planning required during the development of an oil production prospect. The viscosity and volatility of a crude oil may vary quite widely with variations in American Petroleum Institute (API) gravity, particularly with respect to gravities within about the 10°-20° API range. For example, in a typical heavy oil prospect, the change in viscosity which accompanies a change of from 11 to 12 degrees in API gravity is approximately 62 centipoises. However, the change in viscosity as the gravity changes from 18 to 19 degrees API is approximately only 3 centipoises. It is important to determine the oil gravity as precisely as possible and as early as possible in the predevelopment economic studies of an oil production prospect.

Various instruments are used to measure API gravity, such as hydrometers (ATSM D287) and digital density meters (ATSM D7777). However, hydrometers can lead to large uncertainties if used improperly. Digital density meters can provide better reproducibility but require meticulous laboratory skills and must comply with regulation requirements for quality control. In addition, these methods require relatively large volumes of oil, which is not always available. Also, digital density meters are not suitable for extra heavy and heavy crude oils. Due to these issues, it is challenging for laboratories to accurately determine API gravity for their oil samples. Because the API measurement is an industry standard to classify oils, and common laboratory techniques produce high uncertainties, it becomes essential to construct new methods to predict API that would provide higher levels of certainty.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method of determining an API gravity of a crude oil, which includes obtaining a reservoir sample containing the crude oil, separating an aromatic fraction from the reservoir sample, analyzing the aromatic fraction using a gas chromatography mass spectrometry (GC-MS) instrument, determining peak areas of 4-methyldibenzothiophene and 1-methyldibenzothiophene, determining a ratio of 4-methyldibenzothiophene to 1-methyldibenzothiophene based on the peak areas of 4-methyldibenzothiophene and 1-methyldibenzothiophene, and determining the API gravity of the crude oil in the reservoir sample using an empirical correlation between API gravity and the ratio of 4-methyldibenzothiophene to 1-methyldibenzothiophene.

In another aspect, embodiments disclosed herein relate to a method of determining productivity of a region of a reservoir, which includes obtaining a sample from the region of the reservoir, separating an aromatic fraction from the sample, analyzing the aromatic fraction using a gas chromatography mass spectrometry (GC-MS) instrument, determining peak areas of 4-methyldibenzothiophene and 1-methyldibenzothiophene, determining a ratio of 4-methyldibenzothiophene to 1-methyldibenzothiophene based on the peak areas of 4-methyldibenzothiophene and 1-methyldibenzothiophene, determining an API gravity of a crude oil in the sample from the region of the reservoir using an empirical correlation between API gravity and the ratio of 4-methyldibenzothiophene to 1-methyldibenzothiophene, and based on the API gravity of the sample, determining the productivity of the region of the reservoir.

Other aspects and advantages of the claimed subject matter will be apparent from the following description and the appended claims.

DETAILED DESCRIPTION

The API ('American Petroleum Institute') stock-tank oil gravity measurement is an industry standard used to assess the quality of crude oils and can differentiate light oils from heavy oils. This measurement is determined by comparing the density differences of a petroleum fluid to that of the specific gravity of water using the following equation, Equation 1.

$$API \text{ Gravity } (°) = \frac{141.5}{\text{Specific Gravity}} - 131.5 \tag{1}$$

Specific gravity is equal to the density of the oil (measured at 60° F.) divided by the density of water (measured at 60° F.). Heavy crude oils have lower API values and lighter crudes have higher API values, as can be seen in Table 1 (defined by the American Petroleum Institute).

TABLE 1

| Classification of API categories for petroleum oils. | |
| --- | --- |
| API | Oil Classification |
| 0-10° | Extra Heavy Oil |
| 10-22.3° | Heavy Crude Oil |
| 22.3-31.1° | Medium Crude Oil |
| 31.1-45° | Light Crude Oil |
| 45-60° | Condensate |

API gravity is representative of the thermogenic maturity of the fluids and/or their secondary alteration. In the case of maturity, the transformation of the source rock generating the fluids is measured according to different techniques such as vitrinite reflectance, pyrolysis, biomarkers, and molecular compounds. However, not all of these techniques are diagnostic and universally applicable for measuring maturity because they depend on the kerogen type. For example, vitrinite reflectance is a reliable technique for measuring the maturity of terrestrial gas producing Type III kerogen because of the abundance of vitrinite. However, this technique is unreliable for marine Type II kerogen where vitrinite is sparse and instead the HI (mg hydrocarbons/g TOC) from pyrolysis is more essential due to the abundance of oil generating liptinites. Therefore, when utilizing thermal maturity indicators, it is important to constrain to only one kerogen type at a time.

The sulfur content of kerogen (i.e., Type II-S) can also affect the results provided by a thermal maturity indicator. Sulfur-rich kerogen is defined either as S>1.5% or [dibenzothiophene (DBT)/phenanthrene (Phen)]>1. Sulfur lowers the activation energy of kerogen causing hydrocarbon cracking at lower temperatures. This results in oil generation occurring in Type II-S at a lower burial temperature compared to a sulfur-poor Type II kerogen whose activation energy is higher in contrast. The methyldibenzothiophene (MDBT) compounds are a group of sulfur-bearing aromatic hydrocarbons found in high quantities in Type II-S oils, and they are easily identified by gas chromatography-mass spectrometry (GC-MS) techniques.

Figure 1:
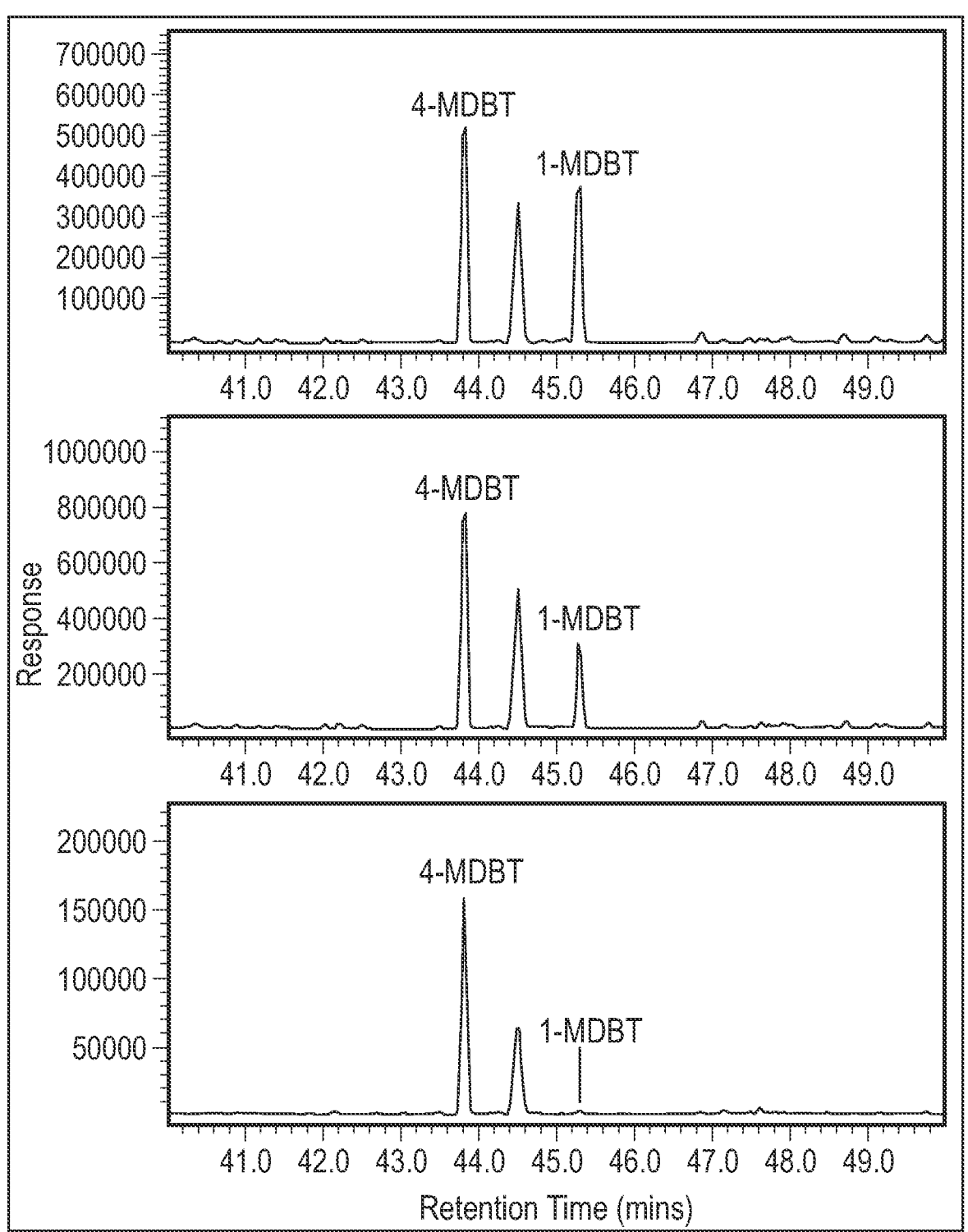
FIG. 1 is a plot of gas chromatography mass spectrometry data showing the change in peak area and height of 4-MDBT and 1-MDBT isomers in low-maturity, medium maturity, and high-maturity oil samples in accordance with one or more embodiments of the present disclosure.

The ratio between the 4-MDBT to 1-MDBT isomers increases with increasing thermal maturity in both Type II-S source rocks and oils. Additionally, the MDBT isomers are still prevalent until at least the end of the wet gas window, making them thermally stable and applicable to assess thermal maturity over large temperature ranges in a basin. FIG. 1 shows how the relative peak areas of the MDBT isomers vary between reservoir samples with differing maturities. As shown in FIG. 1, a more immature sample has a lower ratio of 4-MDBT to 1-MDBT. This ratio increases as the maturity of the sample increases.

Thus, the present disclosure relates to a method of utilizing the aforementioned properties of 4-MDBT to 1-MDBT isomers in order to estimate the API gravity of crude oil. In one or more embodiments, oils sourced from sulfur-rich marine Type II-S kerogen were utilized to develop a relationship between the 4-MDBT/1-MDBT isomer ratio and API gravity. Samples were analyzed with standard chemical laboratory techniques to formulate a calibration curve between these two parameters. By doing so, the API gravity can be directly calculated from the 4-MDBT/1-MDBT ratio obtained from gas chromatography mass spectrometry (GC-MS) analysis, which will provide more reliable and repeatable results for Type II-S oils.

Method of Determining an API Gravity of a Crude Oil

Figure 2:
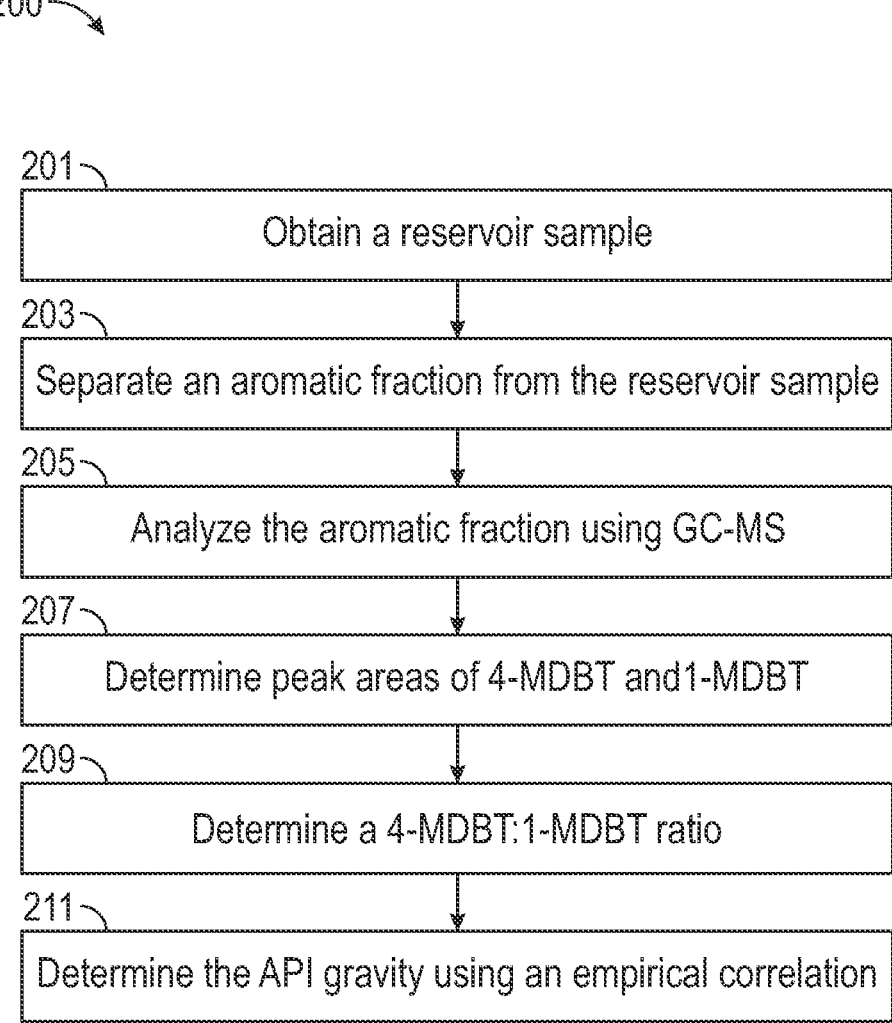
FIG. 2 is a flow diagram of a method of determining an API gravity of a crude oil in accordance with one or more embodiments of the present disclosure.

In one aspect, embodiments disclosed herein relate to a method 200 of determining an API gravity of a crude oil. FIG. 2 is a flow diagram of a method of determining an API gravity of a crude oil in accordance with one or more embodiments of the present disclosure. The method includes obtaining a reservoir sample containing the crude oil, at block 201. Then, an aromatic fraction is separated from the reservoir sample, at block 203. Next, the aromatic fraction is analyzed using a GC-MS instrument, at block 205. The peak areas of 4-methyldibenzothiophene and 1-methyldibenzothiophene are then determined, at block 207. The method then includes determining a ratio of 4-methyldibenzothiophene to 1-methyldibenzothiophene based on the peak areas of 4-methyldibenzothiophene and 1-methyldibenzothiophene, at block 209. The API gravity of the crude oil in the reservoir sample is then determined using an empirical correlation between API gravity and the ratio of 4-methyldibenzothiophene to 1-methyldibenzothiophene, at block 211.

As previously described, embodiment methods include obtaining a reservoir sample containing the crude oil, at block 201. The sample may be obtained from any type of reservoir including conventional and unconventional reservoirs, such as sandstone, limestone, shale and carbonate. The oil may be removed from the reservoir sample using any known means to obtain a liquid crude oil sample for further analysis.

In one or more embodiments, the next step after obtaining the liquid crude oil is to separate the aromatic fraction from the sample, at block 203. Numerous liquid chromatographic separation techniques using various potential substrates or solid-phase extraction techniques may be utilized. For example, in one or more embodiments, a glass pipette column is packed with a suitable substrate, which may include activated silica powder, to perform a typical solid-phase extraction. The substrate is not particularly limited and may be chosen based on which particular samples are being analyzed. Examples of other substrates include alumina, SiOH, and silver. In such embodiments, a solvent suitable to remove the saturate fraction is then passed through the column. A suitable solvent is generally non-polar. An example of the solvent may include, but is not limited to, hexane. This removes the saturate fraction while retaining the asphaltenes, resins, and aromatics in the column. Then, a solvent suitable to remove the aromatic fraction, which may include dichloromethane, is passed through the column. Other suitable solvents or solvent mixtures known in the art may also be used. This removes the aromatic fraction while retaining the resins and asphaltenes on the column.

In one or more embodiments, the separated aromatic fraction is then analyzed using a GC-MS instrument in step 205. Exemplary GC-MS conditions are given in the examples section, however as is understood by those skilled in the art, various conditions may be used in a single quad GC-MS or triple quad GC-MS that can provide data suitable for the methods described herein.

Any suitable GC-MS instrument may be used. For example, in one or more embodiments, the GC-MS instrument may be an Agilent 7890B GC/5977MS or other similar GM-MS instruments.

As is understood by those skilled in the art, a suitable carrier gas and flow rate may be selected such that the carrier gas does not react with any sample components, and it also effectively transports the sample through the column. The carrier gas of one or more embodiments may be helium. However, other carrier gases such as hydrogen and argon may be used. The flow rate of the carrier gas may be selected based on the type, size, and length of the column, as well as the column packing material. For example, in one or more embodiments, the flow rate of the helium carrier gas may have a lower limit of any of 1.0, 1.1, 1.2 and 1.3 mL/min, to an upper limit of any of 1.2, 1.3, 1.4, 1.5 and 1.6 mL/min, where any lower limit can be used in combination with any mathematically compatible upper limit.

The chromatography column used for the analysis may be any column suitable for separating aromatic compounds. For example, in one or more embodiments, the chromatography column may be a DB-5MS (5% phenyl methylpolysiloxane) fused silica capillary column. However, other columns known by those skilled in the art may also be used.

In order to analyze the aromatic fraction via GC-MS, the sample may be heated to a suitable temperature to separate and elute the different fractions. The temperatures and ramp rates may be selected based on the particular sample being run. For example, in one or more embodiments, the sample may be heated to a first temperature ranging from a lower limit of any of 0° C., 10° C., and 20° C. to an upper limit of any of 100° C., 110° C., and 120° C., where any lower limit can be used in combination with any mathematically compatible upper limit. The sample may be held at the first temperature for an amount of time ranging from a lower limit of any of 0 seconds, 30 seconds and 1 minute, to an upper limit of any of 1.5, 2, and 3 minutes where any lower limit can be used in combination with any mathematically compatible upper limit. The temperature may then be increased to a second temperature ranging from a lower limit of any 280° C., 290° C., 300° C., and 310° C. to an upper limit of any of 320° C., 330° C., and 340° C. where any lower limit can be used in combination with any mathematically compatible upper limit. The ramp rate from the first temperature to the second temperature may range from a lower limit of any of 1, 2, and 3° C./min to an upper limit of any of 4, 5, and 6° C./min where any lower limit can be used in combination with any mathematically compatible upper limit. The temperature may then be held at the second temperature for an amount of time ranging from a lower limit of any of 10, 20, 30, 40 or 50 mins to an upper limit of 60, 70, or 80 minutes. The inlet temperature of the GC-MS instrument may have a lower limit of any 280° C., 290° C., 300° C., and 310° C. and an upper limit of any of 320° C., 330° C., and 340° C. where any lower limit can be used in combination with any mathematically compatible upper limit.

The objective of the GC-MS analysis is to obtain a relative concentration of 4-methyldibenzothiophene to 1-methyldibenzothiophene. In one or more embodiments, this is done by analyzing the data from the aforementioned GC-MS sample run to determine the peak areas of 4-methyldibenzothiophene and 1-methyldibenzothiophene by GC-MS analysis, at block 207. This can be done through appropriate analysis using commercially available software to analyze the GC-MS data and determine peak areas. A typical procedure would be to identify the 4-methyldibenzothiophene and 1-methyldibenzothiophene peaks and use the software to auto-integrate the two peaks, then compare the areas to get the 4-methyldibenzothiophene to 1-methyldibenzothiophene ratio. A standard may be employed to obtain the concentrations of 4-methyldibenzothiophene and 1-methyldibenzothiophene.

In one or more embodiments, the method then includes determining a ratio of 4-methyldibenzothiophene to 1-methyldibenzothiophene, at block 209, by dividing the peak area of 4-methyldibenzothiophene by the peak area of the 1-methyldibenzothiophene.

In one or more embodiments, the ratio of 4-methyldibenzothiophene to 1-methyldibenzothiophene is then used to determine the API gravity of the crude oil using an empirical correlation between API gravity and the ratio of 4-methyldibenzothiophene to 1-methyldibenzothiophene, at block 211. The empirical correlation may be predetermined prior to testing samples. For example, in one or more embodiments, prior to analyzing the reservoir sample, a calibration curve may be calculated as the empirical correlation. In such embodiments, different samples having known API gravity values may be analyzed to determine the ratio of 4-methyldibenzothiophene to 1-methyldibenzothiophene. In one or more embodiments, at least ten different reference samples with known API gravity values may be analyzed to provide an empirical correlation. The ratio of 4-methyldibenzothiophene to 1-methyldibenzothiophene obtained may then be plotted as compared to the known API gravity values. An empirical correlation may then be calculated between ratio of 4-methyldibenzothiophene to 1-methyldibenzothiophene and API gravity per ATSM D287. In one or more embodiments, the empirical correlation may be a logarithmic relationship between API gravity and ratio of 4-methyldibenzothiophene to 1-methyldibenzothiophene. This empirical correlation may then be used to determine the API gravity from measured ratios of 4-methyldibenzothiophene to 1-methyldibenzothiophene.

In one or more embodiments, the sulfur-rich crude oils may also be analyzed using hydrometer techniques (from ATSM D287) to obtain density measurements and calculate the absolute API Gravity values using Equation 1.

The generated trendline is a logarithmic equation, Equation 2, with the following general formula:

$$API \text{ Gravity } (°) = a \times \ln\left(\frac{4 - MDBT}{1 - MDBT}\right) + b \tag{2}$$

where 4-MDBT is the peak area of the 4-methyldibenzothiophene, 1-MDBT is the peak area of the 4-methyldibenzothiophene, and where a and b are constants of the logarithmic relationship that may be determined by fitting the data using a logarithmic regression.

This specific values of a and b in equation 2 may change based on different sample sets; however, the general form of equation 2 can apply to all Type II-S oils.

Method of Determining Productivity of a Region of a Reservoir

Figure 3:
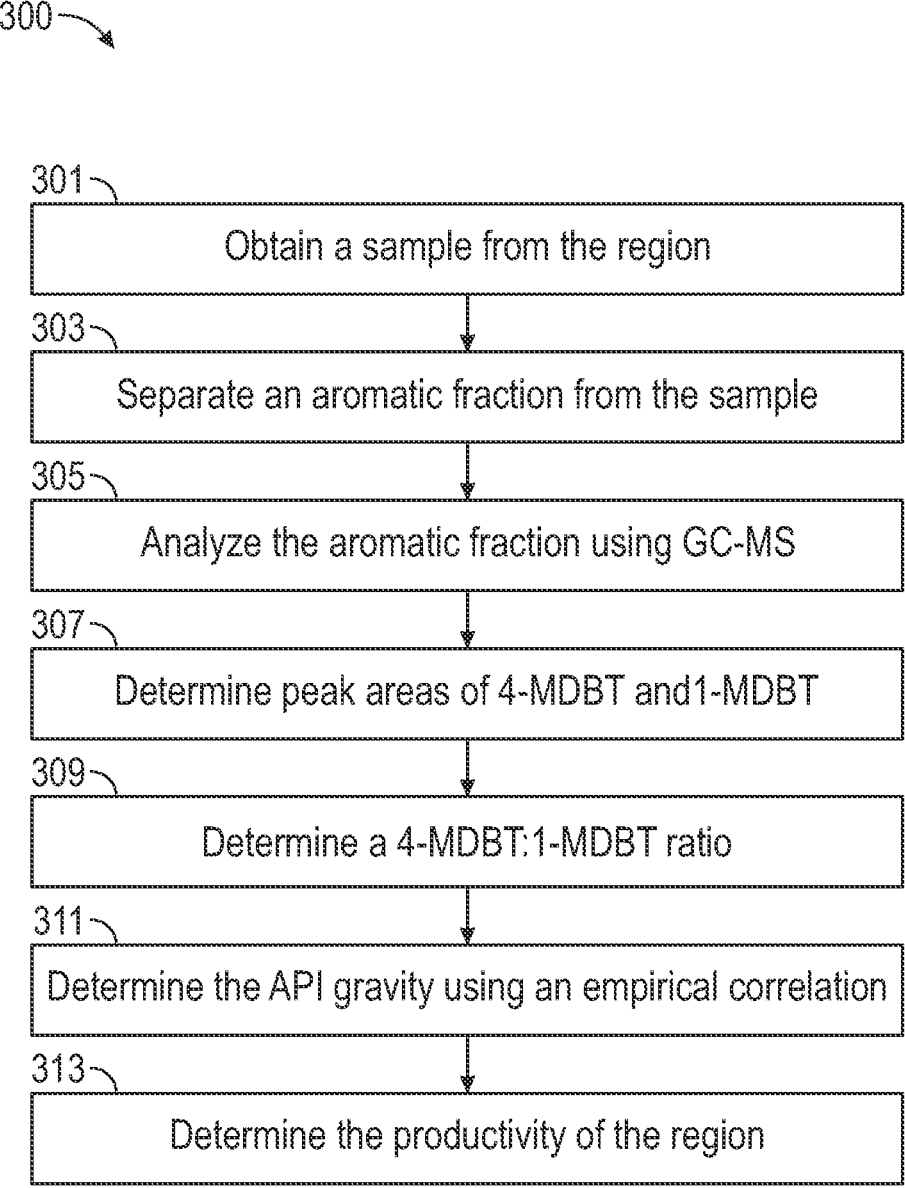
FIG. 3 is a flow diagram of a method of determining productivity of a region of a reservoir in accordance with one or more embodiments of the present disclosure.

In another aspect, embodiments disclosed herein relate to a method of determining the productivity of a region of a reservoir. FIG. 3 is a flow diagram of a method 300 of determining the productivity of a region of a reservoir in accordance with one or more embodiments of the present disclosure. The method includes obtaining a sample from the region of the reservoir, at block 301. Then, an aromatic fraction is separated from the sample, at block 303. The aromatic fraction is then analyzed using a gas chromatography mass spectrometry (GC-MS) instrument, at block 305. The method then includes determining peak areas of 4-methyldibenzothiophene and 1-methyldibenzothiophene, at block 307. The ratio of 4-methyldibenzothiophene to 1-methyldibenzothiophene is then determined based on the peak areas of 4-methyldibenzothiophene and 1-methyldibenzothiophene, at block 309. Then, the API gravity of a crude oil in the sample from the region of the reservoir is determined using an empirical correlation between API gravity and the ratio of 4-methyldibenzothiophene to 1-methyldibenzothiophene, at block 311. The method then includes determining the productivity of the region of the reservoir based on the API gravity of the sample, at block 313.

The initial steps for this method are similar to the method of determining an API gravity of a crude oil detailed above, with the additional step of using the determined API gravity to determine the productivity of the region of the reservoir.

The disclosed method may be particularly useful for well planning purposes. For example, determining the API of hydrocarbons in place may help facilitate planning strategies for oil recovery. During drilling operations, API gravity of samples at different depths can be determined in order to avoid oil recovery efforts in very low API gravity zones (indicative of immovable oil). While the porosity and permeability of a reservoir affect what constitutes immovable oil, in some instances an API gravity value of less than 150 may be indicative of immovable oil. As such, the methods disclosed herein may be used to determine the productivity of certain regions of a well based on the API gravity of different regions. For example, in one or more embodiments, an API gravity value of at least 200 may be indicative of a good productivity region in which hydrocarbons may be readily recovered. Determining the API gravity can inform decisions regarding the chemical makeup of injectants during enhanced oil recovery processes as oils having certain API gravity values may be amenable to certain chemical recovery methods. Similar to a region of immovable oil, a region having an API value of 15° or less may be amenable to certain enhanced oil recovery methods. The methods disclosed herein may also be used to determine when a well should be abandoned. If no hydrocarbons are detected in the sample, then the well may be plugged and abandoned.

Embodiments of the present disclosure may provide at least one of the following advantages. The methods described herein may provide improvements over other methods of determining API gravity. For example, the present method is more reliable at providing accurate data than hydrometers (ATSM D287) and doesn't require meticulous laboratory skills. Methods in accordance with the present disclosure do not require large amounts of an oil sample and is suitable for extra heavy and heavy crude oils. Using methods described herein can allow for determination of API gravity accurately with a small amount of sample, and this API gravity value can be used to assess the productivity of a region in a reservoir.

EXAMPLES

Example GC-MS Conditions:

The following method was used to analyze all oil samples described in the Examples section. 80-100 mg of crude oil was introduced to a glass pipette column prepared using filter paper and filled with activated silica powder. Hexane was then introduced and passed through the pipette column to remove the saturate fraction of the oil while retaining the asphaltenes, resins, and aromatics. Dichloromethane was then introduced and passed through the pipette column to elute and recover the aromatic fraction while retaining the resins and asphaltenes. The MDBT compounds were recovered as a component of the aromatic fraction. The aromatic fraction was then analyzed using a GC-MS instrument to obtain peak information on the 4-MDBT and 1-MDBT isomers. The following GC-MS parameters were used: GC-MS instrument: Agilent 7890B GC/5977MS; carrier Gas: helium; flow rate: 1.2 mL/min; chromatography column: DB-5MS (5% phenyl methylpolysiloxane) fused silica capillary column (60 m×0.32 mm, 0.25 μm thickness); temperature profile: oven held at 90° C. for 1 min, ramped at 3° C./min to 310° C., held isothermal for 50 mins; inlet temperature: 310° C.

Calibration Curve Determination:

The following is an example of how laboratory oil samples were used to construct a calibration curve. 18 high-sulfur oil samples were obtained from comparable sources. Each of the samples was analyzed via GC-MS to obtain the ratio of 4-MDBT/1-MDBT. Each sample was also then analyzed using a hydrometer technique, namely ASTM D287, to obtain density measurements and calculate the APT gravity value for each sample.

Figure 4:
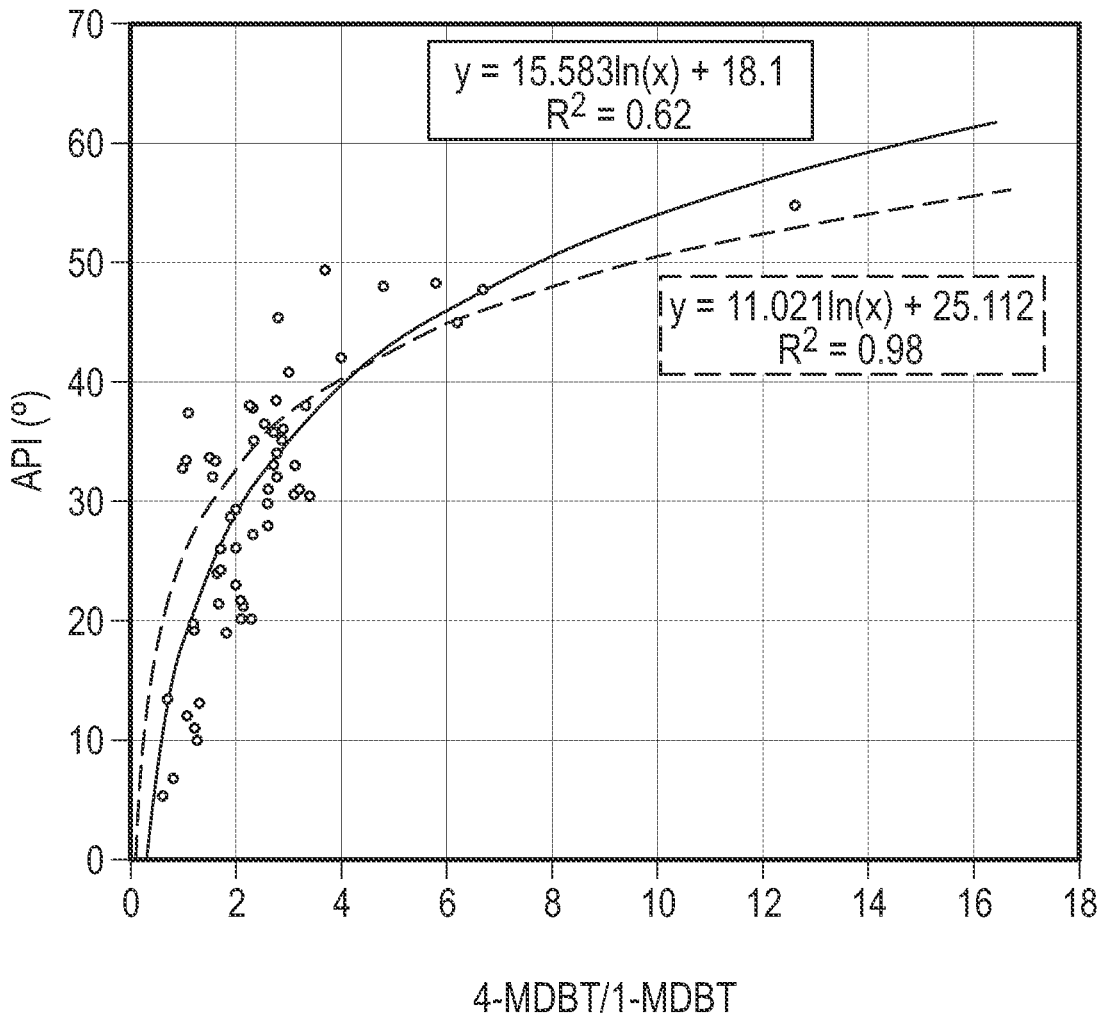
FIG. 4 is a plot of the API gravity vs. 4-MDBT:1-MDBT ratio for a set of laboratory-analyzed sulfur-rich oils and a set of literature sulfur-rich oils in accordance with one or more embodiments of the present disclosure.

FIG. 4 shows the trendline calculated from the correlated API and 4-MDBT/1-MDBT parameters with the dashed line. The trendline has an $R^2$ value that is very close to 1, showing a high degree of fit to the data.

For this unaltered set of S-rich oils, the following equation, Equation 3, was obtained from a logarithmic fit:

$$API \text{ Gravity } (°) = 11.021 \times \ln\left(\frac{4 - MDBT}{1 - MDBT}\right) + 25.112 \qquad (3)$$

To compare to the well-known laboratory samples described above, several literature sources were compiled, and the published 4-MDBT to 1-MDBT ratios of literature samples were used to analyze the literature samples by the same means. The literature sources used to obtain the data were as follows: Wieclaw, D. (2011) Origin of liquid hydrocarbons accumulated in the Miocene strata of the Polish Carpathian foredeep and its Paleozoic-Mesozoic basement. *Annales Societatis Geologorum Poloniae* 81, 443-458; Zhang, S., Huang, H., Su, J., Liu, M., Wang, X., Hu, J. (2015) Geochemistry of Paleozoic marine petroleum from the Tarim Basin, NW China: Part 5. Effect of maturation, TSR and mixing on the occurrence and distribution of alkylbenzothiophenes. *Organic Geochemistry* 86, 5-18; Manshad, A. K., Pashaki, R. S., Ali, J. A., Iglauer, S., Memariani, M., Akbari, M., Keshavarz, A. (2021) Geochemical study of the early cretaceous Fahliyan oil reservoir in the northwest Persian Gulf. *Journal of Petroleum Exploration and Production Technology* 11, 2435-2447; Hegazi, A. H. and Andersson, J. T. (2007) Limitations to GC-MS determination of sulfur-containing polycyclic aromatic compounds in geochemical, petroleum, and environmental investigations. *Energy & Fuels* 21, 3375-3384; Al-Ameri, T. K., Al-Marsoumi, S. W., Al-Musawi, F. A. (2015) Crude oil characterization, molecular affinity, and migration pathways of Halfaya oil field in Mesan Governorate, South Iraq. *Arabian Journal of Geoscience* 8, 7041-7058; Santamaria-Orozco, D., Horsfield, B., Di Primo, R., Welte, D. H. (1998) Influence of maturity on distributions of benzo- and dibenzothiophenes in Tithonian source rocks and crude oils, Sonda de Campeche, Mexico. *Organic Geochemistry* 28, 423-439; Kobraei, M., Rabbani, A., Taati, F. (2019) Upper Jurassic-Lower Cretaceous source-rock evaluation and oil-source rock correlation in the Abadan Plain, Southwest Iran. *Geochemistry International* 57, 790-804; Chiaberge, S., Fiorani, T., Cesti, P. (2011) Methyldibenzothiophene isomer ratios in crude oils: Gas chromatography tandem mass spectrometry analysis. *Fuel Processing Technology* 92, 2196-2201; Abdullah, F. H. and Connan, J. (2002) Geochemical study of some Cretaceous rocks from Kuwait: comparison with oils from Cretaceous and Jurassic reservoirs. *Organic Geochemistry* 33, 125-148.

The literature data is provided as the individual data points in FIG. 4. The compilation of the literature based, oils followed the same generic equation as Equation 2, and generated the following trendline:

$$API \text{ Gravity } (°) = 15.583 \times \ln\left(\frac{4 - MDBT}{1 - MDBT}\right) + 18.100 \qquad (4)$$

The trendline for the literature data, shown as the solid line in FIG. 4, has a lower $R^2$ value than the previous set, 0.62, showing a lower degree of fit to the data. The compiled literature data confirms that the method described herein provides an accurate correlation between the 4-MDBT to 1-MDBT ratio and API gravity.

Various samples with unknown API gravity were analyzed using the GC-MS method described above in order to determine their API gravity values as follows.

Example Oil Sample 1

Oil 1 was analyzed by the above method which determined the 4-MDBT:1-MDBT ratio to be 18.

Using Equation 3:

$$API \text{ Gravity } (°) = 11.021 \times \ln(18) + 25.112$$

$$API \text{ Gravity } (°) = 57$$

Based on this API value, Oil 1 would be considered a condensate.

Example Oil Sample 2

Oil 2 was analyzed by the above method which determined the 4-MDBT:1-MDBT ratio to be 1.5.

Using Equation 3:

$$API \text{ Gravity } (°) = 11.021 \times \ln(1.5) + 25.112$$

$$API \text{ Gravity } (°) = 29$$

Based on this API value, Oil 2 would be considered a medium crude oil.

Example Oil Sample 3

This method of calculating API may compensate for discrepancies caused by chemically altered oils. Oil 3 was analyzed by the above method which determined the 4-MDBT:1-MDBT ratio to be 8. Direct API measurements from a hydrometer give an API of 40.

Using Equation 3:

$$API \text{ Gravity } (°) = 11.021 \times \ln(8) + 25.112$$

$$API \text{ Gravity } (°) = 48$$

In this case, the API gravity has been shifted by 8° which is indicative of oil mixing or secondary alteration (water washing, thermochemical sulfate reduction, evaporative fractionation, or biodegradation).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A method of determining an API gravity of a crude oil, the method comprising:
    obtaining a reservoir sample containing the crude oil;
    separating an aromatic fraction from the reservoir sample;
    analyzing the aromatic fraction using a gas chromatography mass spectrometry (GC-MS) instrument;
    determining peak areas of 4-methyldibenzothiophene and 1-methyldibenzothiophene;

determining a ratio of 4-methyldibenzothiophene to 1-methyldibenzothiophene based on the peak areas of 4-methyldibenzothiophene and 1-methyldibenzothiophene; and
    determining the API gravity of the crude oil in the reservoir sample using an empirical correlation between API gravity and the ratio of 4-methyldibenzothiophene to 1-methyldibenzothiophene.

2. The method of claim 1 further comprising, prior to obtaining the reservoir sample, calculating a calibration curve as the empirical correlation between the API gravity and the ratio of 4-methyldibenzothiophene to 1-methyl-dibenzothiophene.

3. The method of claim 2, wherein the calculating a calibration curve comprises:
    testing at least ten reference samples to determine API Gravity values for each of the at least ten reference samples;
    separating an aromatic fraction from each of the at least ten reference samples;
    analyzing the aromatic fraction from each reference sample using a gas chromatography mass spectrometry (GC-MS) instrument;
    determining peak areas of 4-methyldibenzothiophene and 1-methyldibenzothiophene;
    determining a ratio of 4-methyldibenzothiophene to 1-methyldibenzothiophene in each of the at least ten reference samples based on the peak areas of 4-methyldibenzothiophene and 1-methyldibenzothiophene; and
    calculating a logarithmic regression from the API gravity values and the ratio of 4-methyldibenzothiophene to 1-methyldibenzothiophene of the at least ten reference samples.

4. The method of claim 3, wherein the testing the at least ten reference samples to determine API Gravity values for each reference sample comprises obtaining density measurements and calculating an absolute API Gravity value according to ATSM D287.

5. The method of claim 1, wherein the separating the aromatic fraction from the reservoir sample comprises:
    removing a saturate fraction of the reservoir sample via chromatography to retain asphaltenes, resins, and aromatics;
    eluting the aromatic fraction; and
    recovering the aromatic fraction.

6. The method of claim 1, wherein the empirical correlation between API gravity and the ratio of 4-methyldibenzothiophene to 1-methyldibenzothiophene is logarithmic.

7. The method of claim 1, wherein the crude oil is obtained from a reservoir selected from the group consisting of sandstone, limestone, shale and carbonate.

8. The method of claim 3, wherein the separating the aromatic fraction from the reservoir sample comprises:
    removing a saturate fraction of the reservoir sample via chromatography to retain asphaltenes, resins, and aromatics;
    eluting the aromatic fraction; and
    recovering the aromatic fraction.

9. A method of determining productivity of a region of a reservoir, the method comprising:
    obtaining a sample from the region of the reservoir;
    separating an aromatic fraction from the sample;
    analyzing the aromatic fraction using a gas chromatography mass spectrometry (GC-MS) instrument;
    determining peak areas of 4-methyldibenzothiophene and 1-methyldibenzothiophene;

determining a ratio of 4-methyldibenzothiophene to 1-methyldibenzothiophene based on the peak areas of 4-methyldibenzothiophene and 1-methyldibenzothiophene;

determining an API gravity of a crude oil in the sample from the region of the reservoir using an empirical correlation between API gravity and the ratio of 4-methyldibenzothiophene to 1-methyldibenzothiophene; and based on the API gravity of the sample, determining the productivity of the region of the reservoir.

10. The method of claim 9, wherein separating an aromatic fraction from the sample comprises removing a saturate fraction of the sample via chromatography to retain asphaltenes, resins, and aromatics; eluting the aromatic fraction; and recovering the aromatic fraction.

11. The method of claim 9, wherein the empirical correlation between API gravity and the ratio of 4-methyldibenzothiophene to 1-methyldibenzothiophene ratios is logarithmic.

12. The method of claim 9, wherein the sample is obtained from a reservoir selected from the group consisting of sandstone, limestone, shale and carbonate.

* * * * *